United States Patent
Kim et al.

(10) Patent No.: US 10,339,451 B2
(45) Date of Patent: Jul. 2, 2019

(54) SYSTEM AND METHOD OF DEVELOPING COMPOSITION FOR POWDER MOLDING

(71) Applicant: Kyungpook National University Industry-Academic Cooperation Foundation, Daegu (KR)

(72) Inventors: Ji Sik Kim, Daegu (KR); Kee Sun Sohn, Seoul (KR); Jin Woong Lee, Busan (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 805 days.

(21) Appl. No.: 15/048,600

(22) Filed: Feb. 19, 2016

(65) Prior Publication Data
US 2016/0253589 A1    Sep. 1, 2016

(30) Foreign Application Priority Data
Feb. 27, 2015 (KR) .................... 10-2015-0027798

(51) Int. Cl.
G06N 3/12 (2006.01)
G06F 19/00 (2018.01)
B22F 3/22 (2006.01)

(52) U.S. Cl.
CPC ........... *G06N 3/126* (2013.01); *G06F 19/704* (2013.01); *B22F 3/225* (2013.01)

(58) Field of Classification Search
None
See application file for complete search history.

(56) References Cited

PUBLICATIONS

Chakraborti, Nirupam; Critical Assessment 3: The unique contributions of mulit-objective evolutionary and genetic algorithms in materials research; 2014 Taylor & Francis; Materials Science and Technology, 30:11, 1259-1262. (Year: 2014).*

(Continued)

*Primary Examiner* — Stanley K. Hill
(74) *Attorney, Agent, or Firm* — Norton Rose Fulbright US LLP

(57) ABSTRACT

A system for developing a composition for powder molding which, after a viscosity of the composition for powder molding and a degreasing process, extracts optimal compositional information of the composition in terms of the ratios of the residual binder materials is disclosed. Such a system includes a searching logic unit configured, after generating a plurality of candidate compositional information, to extract the optimal compositional information therefrom and a synthesis/analysis module configured to synthesize and analyze compositions corresponding to the plurality of candidate compositional information and provide to the searching logic unit measurement information on the viscosities of the compositions corresponding to each of the plurality of candidate compositional information and ratios of residual binder materials after a degreasing process. Also, the searching logic unit extracts the optimal compositional information based on the candidate compositional information and the measurement information thereof.

11 Claims, 5 Drawing Sheets

[ALGORITHM 2]

(56) References Cited

PUBLICATIONS

Ahn Seokyoung et al.; Effect of powders and binders on material properties and molding parameters in iron and stainless steel powder injection molding process; Elsevier; Powder Technology 193 (2009) 162-169. (Year: 2009).*

Paszkowicz, Wojciech; Genetic Algorithms, a Nature-Inspired Tool: A Survey of Applications in Materials Science and Related Fields: Part II; Taylor & Francis; Materials and Manufacturing Processes, 28: 708-725, 2013. (Year: 2013).*

Mitra, K.; Genetic algorithms in polymeric material production, design, processing and other applications: a review; Maney; International Materials Reviews 2008, vol. 53, No. 5; pp. 275-297. (Year: 2008).*

Kumar, Deepak et al.; An Investigation on Optimization of Parameters for Injection Molded Polypropylene-Marble Composites with Multi Objective Genetic Algorithm; IEEE International Conference on Recent Advances and Innovations in Engineering, 2016, 6 pages. (Year: 2016).*

Panahi, Ali Keshavarz et al.; Optimization of the Powder Injection Molding Process Parameters Using the Sequential Simplex Algorithm and Sensitivity Analysis; 2013 ASME; Journal of Manufacturing Science and Engineering, vol. 135; 7 pages. (Year: 2013).*

Rao, P. Gangadhara et al.; Parameter Optimization of Al—SiC Metal Matrix Composites Produced using Powder-based Process; International Conference on Robotics, Automation, Control and Embedded Systems—RACE 2015; 5 pages. (Year: 2015).*

\* cited by examiner

[ALGORITHM 1]

[ALGORITHM 2]

[ALGORITHM 3]

SYSTEM AND METHOD OF DEVELOPING COMPOSITION FOR POWDER MOLDING

CROSS-REFERENCE TO RELATED APPLICATION

This application claims priority to and the benefit of Korean Patent Application No. 10-2015-0027798, filed on Feb. 27, 2015, the disclosure of which is incorporated herein by reference in its entirety.

BACKGROUND

1. Field of the Invention

The present invention relates to a system and a method of developing a composition for powder molding capable of extracting compositional information on the composition applied to powder molding such as powder injection molding or powder extrusion molding of metal materials or ceramic materials.

2. Discussion of Related Art

In recent years, a lot of research on powder molding technology such as powder injection molding and powder extrusion molding of various metal materials or ceramic materials has been conducted for mass-producing with low production costs highly functional precision parts with complicated shapes because the precision parts are difficult to manufacture using a conventional molding technology such as a cutting process, precision casting, die casting, powder metallurgy, and the like, or has a price problem.

Generally, powder molding of metal materials or ceramic materials is performed in the order of a process of mixing a binder material with a metal or ceramic powder, a process of subjecting the mixture to injection molding or extrusion molding, a degreasing process of removing the binder material, and a sintering process of strengthening a bond between powders. For the powder molding method for such a metal or ceramic material, development of a powder-binder system for precision parts capable of easy removal of a binder material and exhibiting excellent fluidity for complex manufacturing on a larger scale and miniaturization of powder into finer particles is needed.

However, developments of most materials and processes conducted in the past have been made by very inefficient methods based on trial and error. As a result, these methods have exposed many problems. The most basic problem of the methods based on the conventional trial and error method is that it is practically impossible to search for the proper compositions since basically the range of the compositions to be searched is too wide for developing a binder essential for powder molding. For example, when a new composition for binders is developed by mixing 2 to 5 generally used main materials (lost wax, carnauba wax, polyethylene, polypropylene, polystyrene, etc.) with 2 to 3 auxiliary materials (surfactant, mixed inducing agent, reaction accelerator, etc.), approximately $10^4$ to $10^8$ experimental compositions need to be tested even when the corresponding additives are varied and within a range of 10% and tested, making it practically impossible to test the compositions using the conventional trial and error method. Also, the conventional methods having focused on the research of the compositions themselves, thus neglecting the optimization of subsequent processes such as degreasing, have resulted in the problem where the binder material cannot completely be removed when complex molded products of micro-powder are manufactured on a larger scale or small parts are manufactured using a nano-powder.

Therefore, to develop a composition for powder molding a metal or ceramic material that ensures a technical foundation for manufacturing complex products, there is an urgent need for a system for developing a novel binder material capable of overcoming the limitations of a strategy for developing a binder material depending on a trial and error method with no principles or impractical theoretical calculations and compensating for the drawbacks of these two approaches.

SUMMARY OF THE INVENTION

The present invention is directed to a system and method of developing a composition for powder molding capable of effectively developing a composition powder molding in a short period of time by extracting compositional information on candidate compositions using a genetic algorithm and combining actually synthesized and analyzed information with the extracted compositional information.

According to an aspect of the present invention, there is provided a system for developing a composition for powder molding capable of extracting compositional information on the composition in terms of a viscosity of the composition for powder molding and ratios of residual binder materials after a degreasing process. Such a system for developing a composition for powder molding may include a searching logic unit configured to generate a plurality of candidate compositional information and extract the optimal compositional information from the plurality of candidate compositional information, and a synthesis/analysis module configured to synthesize and analyze compositions corresponding to the plurality of candidate compositional information and provide measurement information on viscosities of the compositions corresponding to each of the plurality of candidate compositional information, and ratios of residual binder materials after a degreasing process to the searching logic unit. Here, the searching logic unit may extract the optimal compositional information based on the candidate compositional information and the measurement information on the candidate compositional information.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as generally understood by a person skilled in the related art to which the present invention belongs. In general, the nomenclatures used in this specification and the experimental methods described below are widely known and generally used in the related art.

A system for developing a composition for powder molding according to one exemplary embodiment of the present invention may be used to extract optimal compositions from predetermined binder materials in a powder molding method such as powder injection molding or powder extrusion molding of metal materials or ceramic materials.

Generally, a mixture obtained by mixing a main binder including at least one material selected from thermoplastic polymer materials such as polyethylene, polypropylene, polystyrene, ethylene vinyl acetate, and the like, a secondary binder selected from wax materials such as polyethylene wax, paraffin wax, carnauba wax, and the like, and one or more process formulations selected from a surfactant, a mixing inducing agent, a reaction accelerator, and the like may be used as a binder material for powder molding of a metal powder or a ceramic powder.

According to one exemplary embodiment of the present invention, the system for developing a composition for powder molding may, after specifying component materials included in powder and binder materials, extract optimal compositions of the respective components for powder molding in terms of viscosity of the composition for powder molding, ratios of residual binder materials after a degreasing process, etc. The viscosity of the composition is a factor having the greatest influence on molding characteristics, and the ratio of the residual binder material after the degreasing process is a factor having the greatest influence on mechanical properties of sintered moldings Hereinafter, the system for developing a composition for powder molding according to one exemplary embodiment of the present invention will be described with reference to FIGS. 1 to 5.

Figure 1:
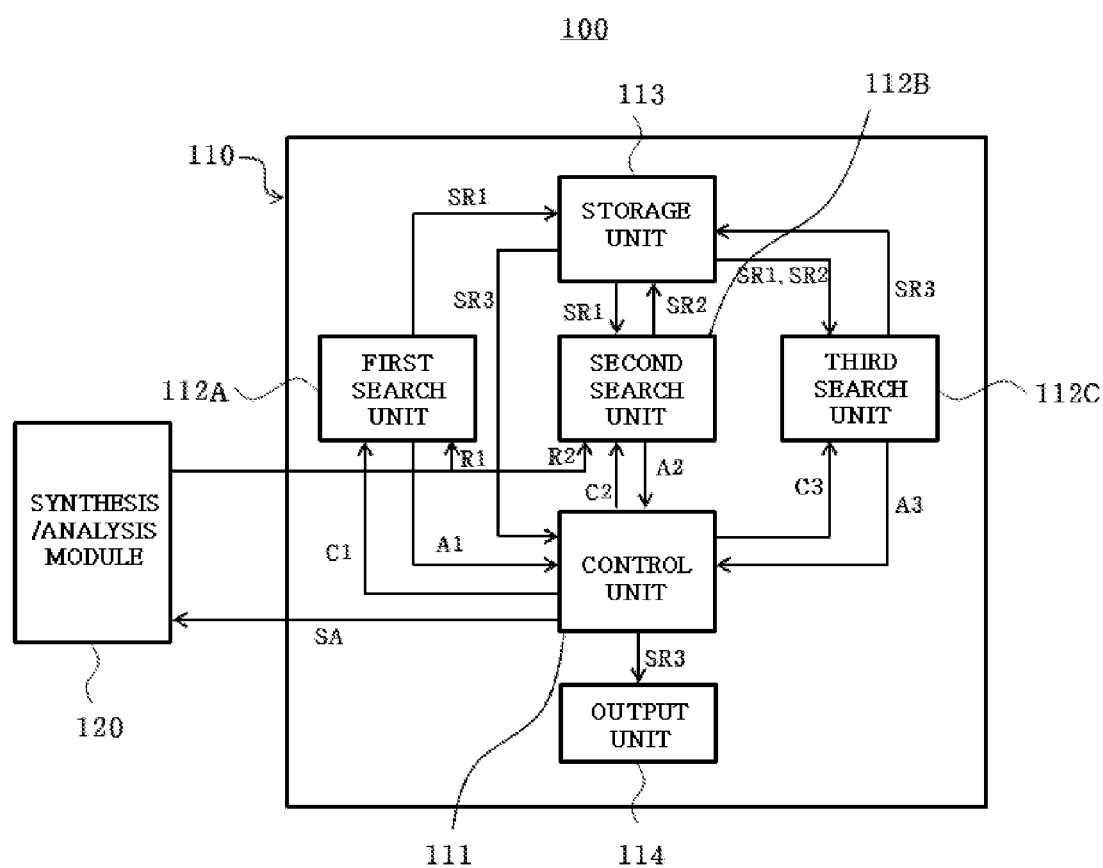
FIG. 1 is a diagram for describing a system for developing a composition for powder molding according to one exemplary embodiment of the present invention.
Figure 2:
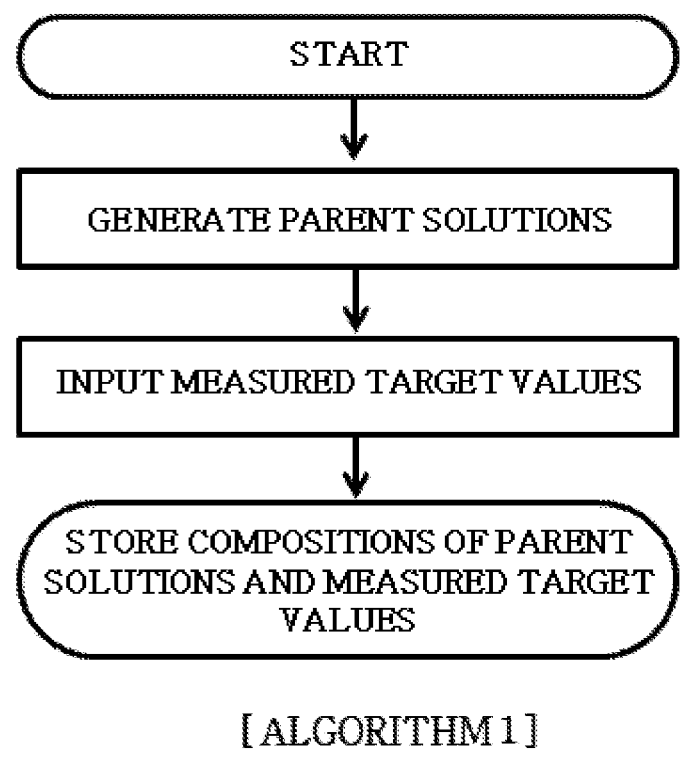
FIGS. 2 to 4 are each diagrams showing algorithms for describing functions of first to third search units shown in FIG. 1.
Figure 3:
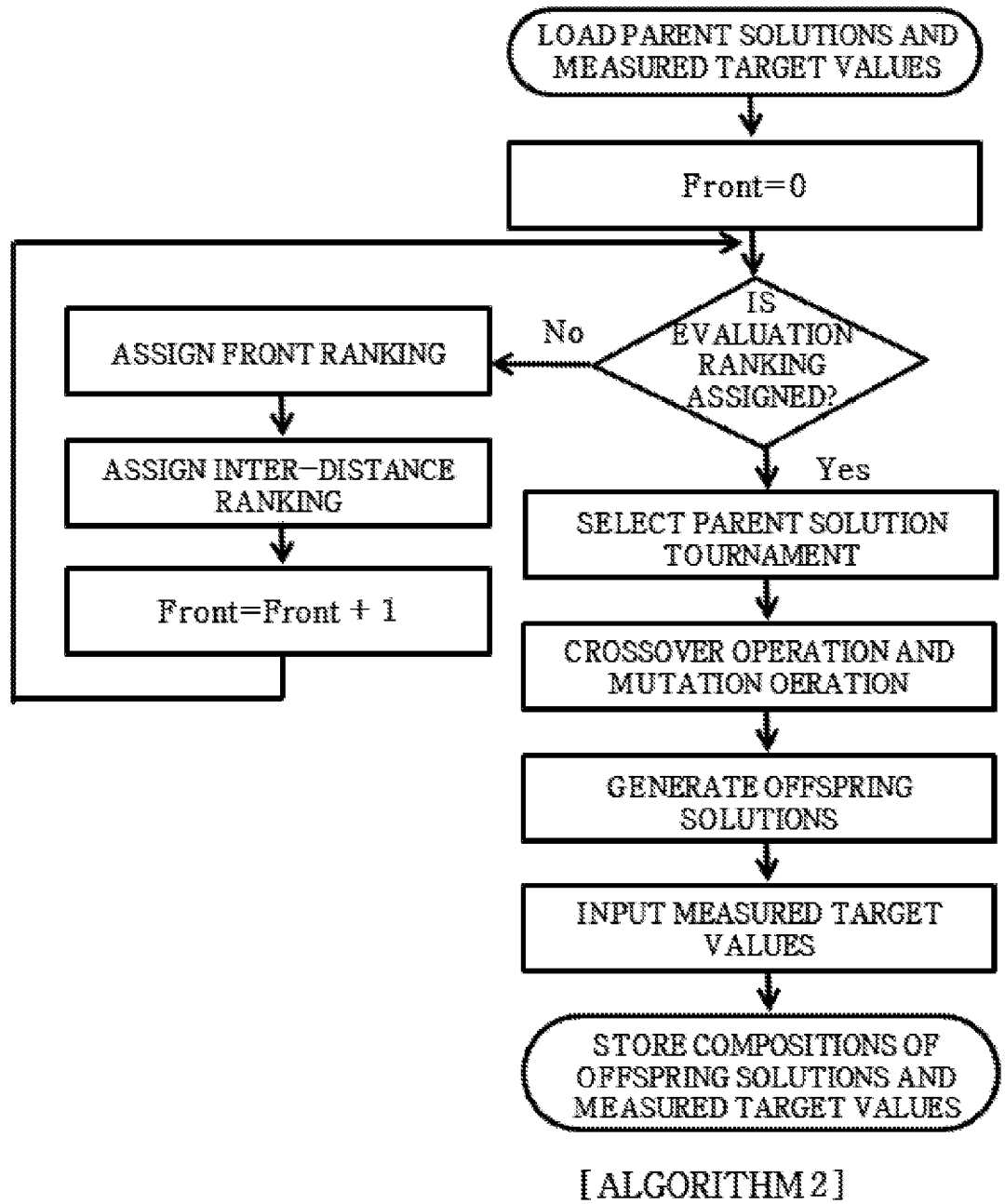
Figure 4:
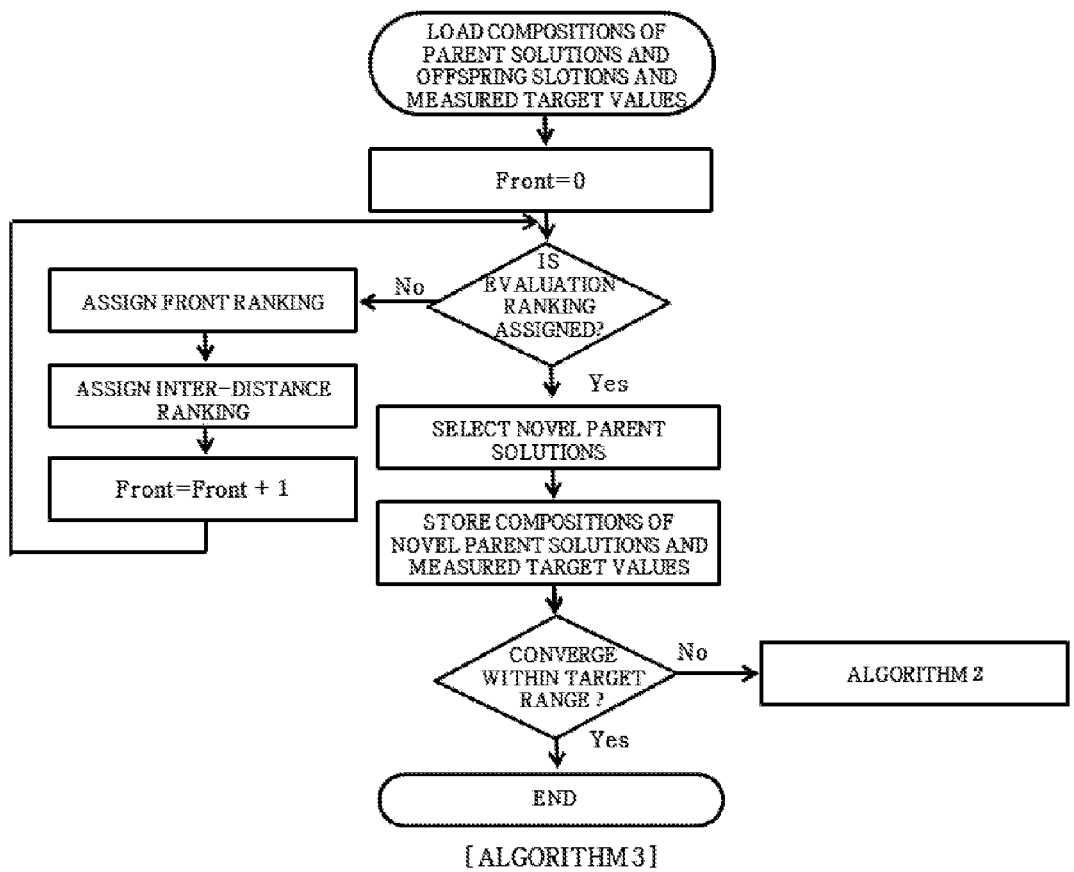

FIG. 1 is a diagram for describing a system for developing a composition for powder molding according to one exemplary embodiment of the present invention, and FIGS. 2 to 4 are each diagrams showing algorithms for describing functions of first to third search units shown in FIG. 1.

Referring to FIGS. 1 to 4, the system 100 for developing a composition for powder molding according to one exemplary embodiment of the present invention may include a searching logic unit 110 and a synthesis/analysis module 120.

The searching logic unit 110 may include a control unit 111, first to third search units 112A, 112B and 112C, a storage unit 113, and an output unit 114.

The first search unit 112A may be driven by a first control signal C1 from the control unit 111 and generate 'N' first parent solutions according to a first algorithm as shown in FIG. 2 and store in the storage unit 113. Each of the 'N' first parent solutions may include specific compositional information on the compositions for powder molding composed of predetermined component materials, and the first search unit 112A may randomly generate the 'N' first parent solutions.

When the 'N' first parent solutions are generated by the first search unit 112A may, after the synthesis/analysis module 120 synthesizes compositions corresponding to each of the 'N' first parent solutions according to an analysis command signal SA of the control unit 111, analyze characteristics of each thereof such as viscosities and ratios of residual binder materials after a degreasing process and provide the analysis results to the first search unit 112A. That is, the synthesis/analysis module 120 may provide to the first search unit 112A measured target values R1 including the measurement information on the viscosities of the compositions corresponding to each of the 'N' first parent solutions and the ratios of the residual binder materials after the degreasing process. Also, the first search unit 112A may store in the storage unit 113 the measured target values with the 'N' first parent solutions, that is, a combination SR1 of the first parent solutions and the measured target values thereof.

When the combination SR1 of the 'N' first parent solutions and the measured target values corresponding to each thereof are stored in the storage unit 113, the second search unit 112B may generate first offspring solutions according to an algorithm 2 as shown in FIG. 3. Each of the first offspring solutions may also include specific compositional information on the compositions for powder molding composed by the predetermined component materials. According to one exemplary embodiment, the second search unit 112B may, after first drawing the combination SR1 of the 'N' first parent solutions and the measured target values corresponding to each thereof from the storage unit 113 according to a second control signal C2 from the control unit 111, assign evaluation rankings to each of the first parent solutions. Specifically, the second search unit 112B may assign the evaluation rankings to the 'N' first parent solutions using the measured target values.

Figure 5:
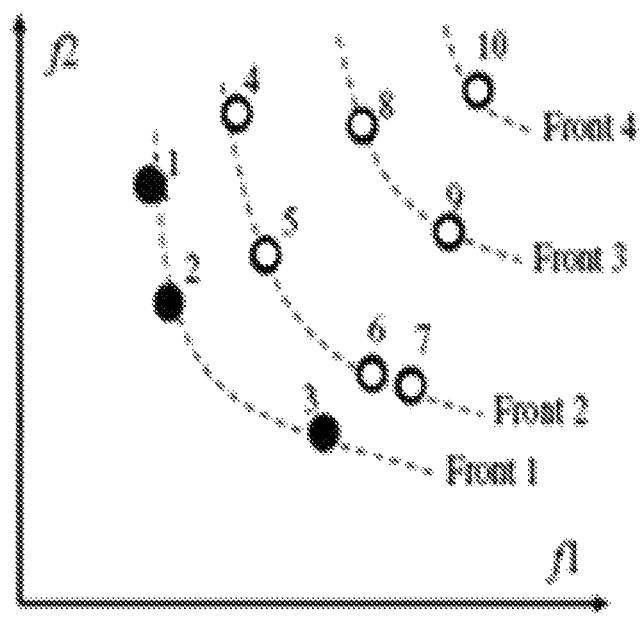
FIG. 5 is a diagram for describing evaluation rankings of candidate compositional information.

According to one exemplary embodiment, the second search unit 112B may, after aligning the 'N' first parent solutions in a plane defined by parameters corresponding to the target values, compare each of the first parent solutions against each other to determine a dominance relation, thereby assign the front ranking to each of the first parent solutions. For example, when 10 first parent solutions are aligned in a plane defined by a parameter f1 corresponding to the 'viscosity of the composition' and a parameter f2 corresponding to the 'ratios of the residual binder materials after a degreasing process' as shown in FIG. 5, a first front ranking (Front 1) may be assigned to the non-dominant first parent solutions '1', '2' and '3' of the innermost positions. Thereafter, depending on the strength of the dominance, a second front ranking (Front 2) may be assigned to the first parent solutions '4', '5', '6' and '7,' a third front ranking (Front 3) may be assigned to the first parent solutions '8' and '9,' and a fourth front ranking (Front 4) may be assigned to the first parent solution '10,'. Subsequently, in the plane defined by the parameters corresponding to the target values, the second search unit 112B may, after calculating inter-distance between each of the first parent solutions according to each of front rankings, assign the inter-distance to each of the first parent solutions according to the inter-distance rankings. According to one exemplary embodiment, an inter-distance for the '$i^{th}$' first parent solution may be defined as an average of distances between the '$i^{th}$' first parent solution and the '$i-1^{st}$' and '$i+1^{st}$' first parent solutions adjacent to the '$i^{th}$' first parent solution in the plane. As described above, when the front rankings and the inter-distance rankings are assigned to the 'N' first parent solutions, evaluation rankings for the 'N' first parent solutions may be primarily determined by the front rankings and may be determined by the inter-distance rankings in the case of duplicate front rankings.

After the evaluation rankings are assigned to each of the 'N' first parent solutions, the second search unit 112B may generate 'N' first offspring solutions by performing a 'crossover' operation and a 'mutation' operation on the first parent solutions selected from the 'N' first parent solutions in a tournament manner using the evaluation rankings. Crossover operations and mutation operations applied to known genetic algorithms may be used as the 'crossover operation' and the 'mutation operation' without limitation, and thus a detailed description thereof will be omitted.

When the 'N' first offspring solutions are generated by the second search unit 112B, the synthesis/analysis module 120 may, after synthesizing compositions corresponding to each of the 'N' first offspring solutions according to the analysis command signal SA from the control unit 111, analyze and then provide measured target values of each thereof to the second search unit 112B. Thereafter, the second search unit 112B may store a combination SR2 of the 'N' first offspring solutions and the measured target values in the storage unit 113.

When the combination SR2 of the 'N' first offspring solutions and the corresponding measured target values thereof is stored in the storage unit 113, the third search unit 112C may select the second parent solution according to an algorithm 3 shown in FIG. 4 and determine whether convergence thereof within target range is achieved. According to one exemplary embodiment, the third search unit 112C may, after drawing the combination SR1 of the 'N' first parent solutions and the measured target values corresponding to each thereof and the combination SR2 of the 'N' first offspring solutions and the measured target values corresponding to each thereof from the storage unit 113 depending on a third control signal C3 from the control unit 111, assign to the 'N' first parent solutions and the 'N' first offspring solutions new evaluation rankings among thereof. In this case, the evaluation rankings is assigned in substantially the same manner as described above, and thus a detailed description thereof will be omitted.

After the evaluation rankings are assigned to each of the 'N' first parent solutions and the 'N' first offspring solutions, the third search unit 112C may select the 'N' second parent solutions from the 'N' first parent solutions and the 'N' first offspring solutions based on the evaluation rankings and may store a combination SR3 of the second parent solutions and measured target values thereof in the storage unit 113.

Meanwhile, when the measured target values for the second parent solutions converge within a preset target range, the control unit 111 may output to the output unit 114 the second parent solutions as the optimal compositions for powder molding, and terminate the operation of the system 100.

On the other hand, when the measured target values for the second parent solutions do not converge within the target range, the second search unit 112B may, depending on a control signal C2 from the control unit 111, generate 'N' second offspring solutions based on the 'N' second parent solutions, which is then stored with the measured target values for the second offspring solutions provided from the synthesis/analysis module 120. Thereafter, the third search unit 112C may select 'N' third parent solutions from the storage unit 113 in the same manner as described above for the 'N' second parent solutions and the 'N' second offspring solutions, which is then stored with the measured target values in the storage unit 113.

Also, when the measured target values for the third parent solutions converge within the target range, the control unit 111 may output the third parent solutions as the optimal compositions for powder molding. However, when the measured target values for the third parent solutions do not converge within the target range, the above-described operations may be repeatedly performed.

According to the exemplary embodiments of the present invention, since the optimal compositions for powder molding may be extracted by combining the target value measured by experiments with the compositional information generated by calculations using a computer, a wide range of compositions which have not been searched in conventional studies may be optimized within a short period of time with minimum effort.

According to the exemplary embodiments of the present invention, the optimal compositional information on the compositions for powder molding can be effectively extracted within a short period of time by evolving the initially generated compositional information using the genetic algorithm and using the information actually measured by the synthesis/analysis module.

It will be apparent to those skilled in the art that various modifications can be made to the above-described exemplary embodiments of the present invention without departing from the scope of the invention. Thus, it is intended that the present invention covers all such modifications provided they come within the scope of the appended claims and their equivalents.

What is claimed is:

1. A system for developing a composition for powder molding capable of extracting optimal compositional information on the composition in terms of a viscosity of the composition for powder molding and ratios of residual binder materials after a degreasing process, the system comprising:
    a searching logic unit configured to generate a plurality of candidate compositional information and extract the optimal compositional information from the plurality of candidate compositional information; and
    a synthesis/analysis module configured to synthesize and analyze compositions corresponding to the plurality of candidate compositional information and provide measurement information on viscosities of the compositions which correspond to each of the plurality of candidate compositional information, and ratios residual of binder materials after a degreasing process to the searching logic unit,
    wherein the searching logic unit extracts the optimal compositional information based on the candidate compositional information and the measurement information thereof.

2. The system of claim 1, wherein the candidate compositional information comprises a plurality of first parent solutions and a plurality of first offspring solutions, and
    the searching logic unit comprises:
    a first search unit configured to randomly generate the first parent solutions;
    a second search unit configured to generate the plurality of first offspring solutions from the first parent solutions based on the measurement information on each of the first parent solutions; and
    a third search unit configured to select a plurality of second parent solutions from the first parent solutions and the first offspring solutions based on the measurement information on each of the first parent solutions and the first offspring solutions.

3. The system of claim 2, wherein the searching logic unit further comprises a control unit configured to control operations of the first and second search unit and the synthesis/analysis module, and the control unit outputs the second parent solutions as the optimal compositional information when the measurement information on the second parent solutions converges within a preset target range.

4. The system of claim 3, wherein, when the measurement information on the second parent solutions does not converge within the preset target range, the second search unit generates a plurality of second offspring solutions from the second parent solutions based on the measurement information on each of the second parent solutions, the synthesis/analysis module provides measurement information corresponding to each of the second offspring solutions to the second search unit, and the third search unit selects a plurality of third parent solutions from the second parent solutions and the second offspring solutions based on the measurement information on each of the second parent solutions and the second offspring solutions.

5. The system of claim 4, wherein, when the measurement information on the third parent solutions converges within the target range, the control unit outputs the third parent solutions as optimal compositional information, and when the measurement information on the third parent solutions does not converge within the target range, the control unit repeatedly runs the second and third search unit until the compositional information selected by the third search unit converges within the target range.

6. The system of claim 5, wherein the first offspring solutions are generated through a crossover operation and a mutation operation based on the first parent solutions and the measurement information on each thereof, and the second offspring solutions are generated through a crossover operation and a mutation operation based on the second parent solutions and the measurement information on each thereof.

7. The system of claim 2, wherein the searching logic unit further comprises a storage unit configured to store the candidate compositional information and the measurement information on each thereof.

8. A method of developing a composition for powder molding capable of extracting optimal compositional information on the composition in terms of a viscosity of the composition for powder molding and ratios of residual binder materials after a degreasing process, the method comprising:

randomly generating 'N' first parent solutions, synthesizing and analyzing compositions corresponding to each of the first parent solutions and generating measurement information on viscosities of the compositions and ratios of residual binder materials after a degreasing process (first step);

generating 'N' first offspring solutions from the first parent solutions based on the first parent solutions and the measurement information thereon, synthesizing and analyzing compositions corresponding to each of the first offspring solutions and generating measurement information on viscosities of the respective compositions and ratios of residual binder materials after a degreasing process (second step); and selecting 'N' second parent solutions based on the first parent solutions and the measurement information thereon and the first offspring solutions and the measurement information thereon, and determining whether the measurement information on the 'N' second parent solutions converges within a preset target range (third step), wherein, when the measurement information on the second parent solutions converges within the preset target range, the second parent solutions are output as the optimal compositional information, and when the measurement information on the second parent solutions does not converge within the preset target range, the second and third steps are repeatedly performed based on the second parent solutions.

9. The method of claim 8, wherein the 'N' first offspring solutions are generated by performing crossover operations and mutation operations for each of the first parent solutions selected from the first parent solutions according to evaluation rankings based on the measurement information on the first parent solutions.

10. The method of claim 8, wherein the 'N' second parent solutions are selected according to the evaluation rankings based on the measurement information on the first parent solutions and the measurement information on the first offspring solutions.

11. The method of claim 10, wherein the evaluation rankings are determined by front rankings assigned according to a dominance relation in a plane defined by parameters corresponding to the viscosities and the ratios of the residual binder materials after the degreasing process, and inter-distance rankings assigned according to an inter-distance in the plane.

* * * * *